United States Patent [19]

Agbo et al.

[11] Patent Number: 5,445,836
[45] Date of Patent: Aug. 29, 1995

[54] ENZYMATIC CLARIFICATION OF TEA EXTRACTS

[75] Inventors: Francis Agbo, Warwick; Joseph E. Spradlin, Monroe, both of N.Y.

[73] Assignee: Kraft Foods, Inc., Northfield, Ill.

[21] Appl. No.: 241,832

[22] Filed: May 12, 1994

[51] Int. Cl.$^6$ .............................................. A23F 3/20
[52] U.S. Cl. ...................................... 426/52; 426/597
[58] Field of Search ................................ 426/52, 597

[56] References Cited

U.S. PATENT DOCUMENTS

| | | | |
|---|---|---|---|
| 3,812,266 | 5/1974 | Sanderson et al. | 426/52 |
| 3,959,497 | 5/1976 | Takino | 426/52 |
| 4,051,267 | 9/1977 | Jongeling | 426/330.3 |
| 4,109,057 | 8/1978 | Nakamura et al. | 428/528 |
| 4,639,375 | 1/1987 | Tsai | 426/49 |
| 4,748,033 | 5/1988 | Syfert et al. | 426/330.3 |
| 5,043,176 | 8/1991 | Bycroft et al. | 426/335 |
| 5,258,188 | 11/1993 | Barmentlo et al. | 426/52 |

OTHER PUBLICATIONS

*Enzymes In Food and Beverage Processing*, 1977 Chapter 2, pp. 12–16, Sanderson et al.: "Use of Enzymes in the Manufacture of Black Tea and Istant Tea".

*Primary Examiner*—Joseph Golian
*Attorney, Agent, or Firm*—Thomas A. Marcoux; Thomas R. Savoie

[57] ABSTRACT

A process for producing a tea extract which forms little or no haze when stored at refrigeration temperatures. The process comprises incubating a mixture of oxidase, tannase and tea extract, and then separating insoluble solids from the tea extract. The tea extract is preferably a concentrate which is subsequently diluted to provide a ready-to-drink beverage. Haze which develops on cold storage of the extract or of tea beverages prepared from the extract is significantly reduced.

21 Claims, 1 Drawing Sheet

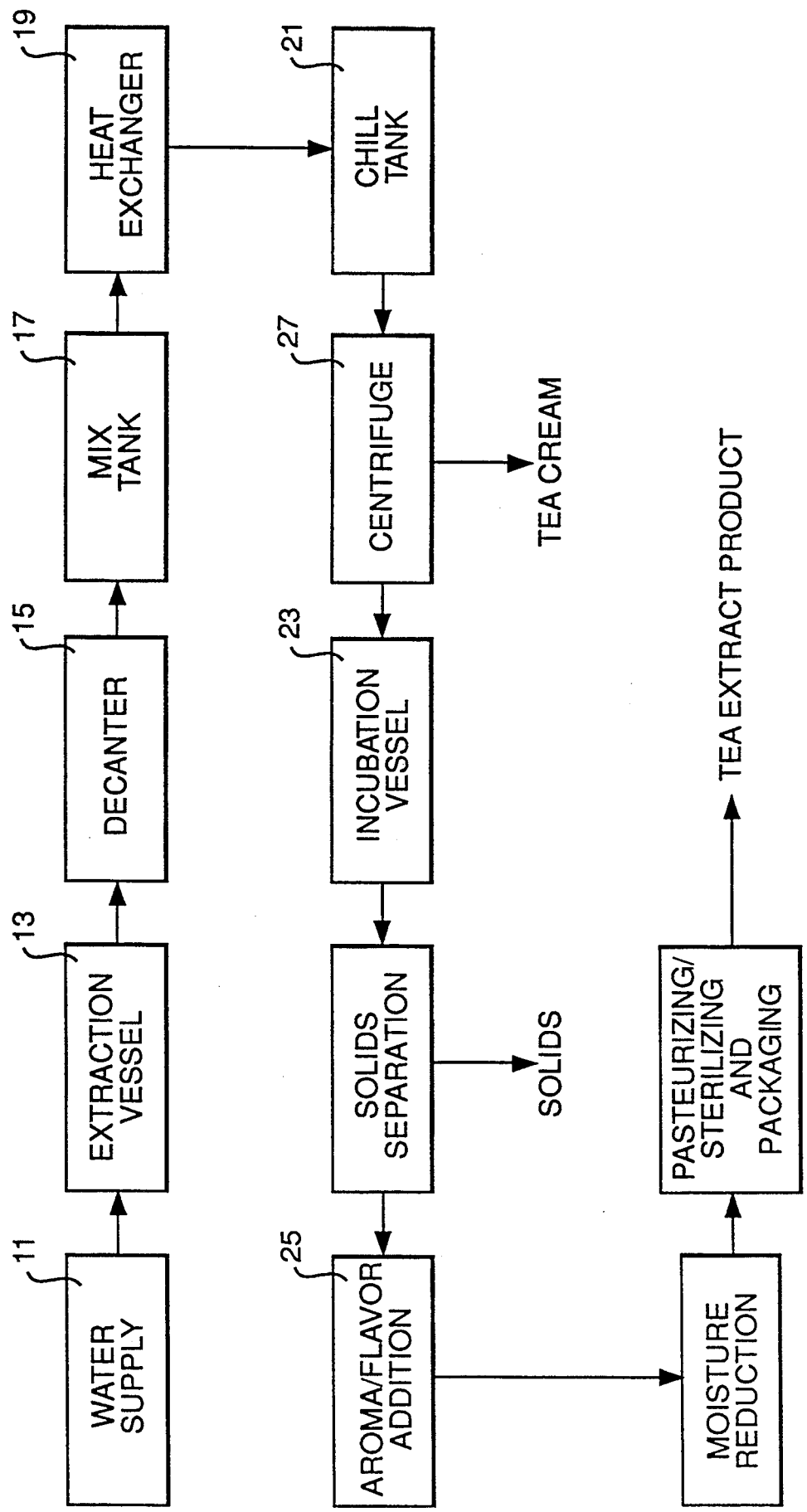

ENZYMATIC CLARIFICATION OF TEA EXTRACTS

FIELD OF THE INVENTION

The present invention relates to a method of producing a tea beverage and, more particularly, to the enzymatic treatment of a tea extract with oxidase and tannase to produce tea extract which forms little or no haze when stored at refrigeration temperatures, and to tea extracts so produced.

BACKGROUND OF THE INVENTION

Instant tea beverages are typically available to consumers as a canned or bottled, single-strength beverage ready for consumption or as a concentrate which is diluted with water to form a drinkable tea beverage. Tea extracts are prepared commercially by extraction of the leaves with water at elevated temperature and then separating the aqueous tea extract, usally a concentrate, from the leaves. The separated tea extract contains both soluble and insoluble tea solids and must undergo a series of additional processing steps to reduce the amount of insoluble solids. Conventional methods of removing insoluble tea solids are known as decreaming processes and utilize adjustments in process variables, such as temperature, to cause precipitation of the insoluble tea solids, followed by centrifugation, filtration or other equivalent techniques to remove precipitate complexes.

Conventional decreaming processes are described in Takino, U.S. Pat. No. 3,959,497, which relates to the use of tannase to provide a decreamed tea concentrate which provides a tea of improved astringency and color without turbidity. Takino notes that cream solids removed by conventional decreaming contain desirable tea color and astringency. Takino treats the cream solids with tannase to recover tea color and astringency. Takino discloses treatment of the tea extract either prior to or after centrifugation to remove the cream and also disclose treatment of the separated cream.

We have found that tea extracts which are decreamed by conventional techniques will develop considerable haze when stored under refrigeration. The development of haze is relatively more rapid in a tea concentrate and is less rapid in ready-to-drink tea beverages. We have found that incubation with tannase as disclosed by Takino does not significantly reduce such refrigeration-developed haze.

It is an object to provide aqueous tea extracts, particularly aqueous tea concentrates, in which development of haze upon storing under refrigeration is reduced.

It is a further object to provide such extracts in which such haze development is significantly less than results from treatment with tannase alone.

SUMMARY OF THE INVENTION

The foregoing and other objects which will be apparent to those skilled in the art are achieved in accordance with the invention by providing a process for producing a tea extract which forms a reduced amount of haze when stored under refrigeration comprising the steps of (a) adding oxidase and tannase to an aqueous tea extract; (b) incubating the extract; and (c) separating insoluble solids from the incubated extract, the oxidase and tannase being added in amounts sufficient to reduce formation of haze caused by storing the extract under refrigeration to an extent substantially greater than that achieved by addition of tannase alone.

BRIEF DESCRIPTION OF THE DRAWING

The drawing is a diagrammatic flow sheet of a process for producing a tea extract in accordance with the present invention.

DETAILED DESCRIPTION OF THE PREFERRED EMBODIMENTS

Referring now to the drawing, a process for producing a tea extract in accordance with the present invention is shown. Tea leaves are first contacted with water from water supply vessel 11 at an elevated temperature in a conventional extraction vessel 13 to provide an aqueous tea extract. The source of the leaves may be fermented or unfermented tea leaves, such as black tea, oolong tea, green tea, or mixtures thereof. The mixture has particular applicability to black tea, and, accordingly, black tea is preferred. The tea leaves are typically slurried with water from a distilled water source 11.

Generally, the amount of water and the conditions of extraction are conventional and are such as to yield an aqueous extract having at least the concentration of a ready-to-drink beverage and preferably to yield an aqueous tea concentrate suitable for dilution with water to provide a ready-to-drink beverage. For producing a ready-to-drink tea extract, the amount of water will generally be from 94 to 99% and preferably from 98 to 99% by weight based on the weight of the tea leaves. For producing a tea concentrate, the amount of water added will generally be from 70 to 90% and preferably from 83 to 88% by weight based on the weight of the tea leaves. The water used for extraction is potable and is preferably distilled. The soluble tea solids content of a ready-to-drink aqueous tea extract is generally from 0.3 to 1.5% and preferably from 0.5 to 1.0% by weight based on the weight of the beverage. The soluble tea solids content of a concentrate is preferably about 5 to 15, more preferably 8-12, times that of a tea beverage or about 3-15%, preferably 4-10%, by weight based on the weight of the concentrate.

Extraction may be carried out in conventional equipment. The equipment may be of the continuous, semicontinuous or batch type such as a jacketed batch vessel 13 shown in the drawing. Extraction conditions are also conventional and may be carried out at atmospheric or elevated pressure.

The temperature of the extraction water is preferably at least about 190° F. to effect optimum extraction of the tea from the leaves. Extraction time is generally at least 5 or 10 minutes and preferably from 5–30 minutes. Conventional additives are preferably added to the water in extraction tank 13. Suitable chelating agents include EDTA are polyphosphates and are employed to sequester undesirable minerals, such as calcium and magnesium, which are typically present in hard water and tea leaves. If desired, tea aroma and flavor components (e.g., distillates) can be volatilized from the extract, collected, condensed and returned to the extract at a later step in the process.

The tea extract is separated from the tea leaves in a decanter 15 or in other suitable separation equipment such as a filter, and passes to a mix tank 17 where pH may be adjusted and where various conventional ingredients may be added. pH of the extract is preferably about 4–7 and more preferably about 5–6. Suitable additives include tannic acid, phosphoric acid, and dried tea concentrate flavor. The resulting tea extract is preferably stirred for a sufficient time to achieve uniformity, suitably about 10 minutes. The tea extract is then subjected to conventional decreaming steps which include chilling the tea extract to precipitate insoluble tea solids or tea cream and then utilizing separation equipment to remove the solids. In a preferred decreaming process, the tea extract is passed into a chill tank 21 where the tea extract is cooled to a temperature of about 45° F. or less, preferably in the range of about 33°-40° F., to cause precipitation of insoluble tea solids or tea creams. Temperature may first be reduced rapidly by passing the tea extract through a heat exchanger 19. The tea extract is preferably cooled for at least 1 hour. Removal of the tea cream is typically achieved using a centrifuge 27, though other suitable solids separation equipment, such as a filter, may be utilized. Preferably the soluble tea solids comprise 0.5-15% by weight of the resulting decreamed tea extract.

The tea extract then passes to an incubation vessel 23 where it is treated with oxidase and tannase in accordance with the invention. Preferably, the oxidase is a sugar oxidase. Even more preferably, the oxidase is selected from mannose oxidase, glucose oxidase and galactose oxidase. The oxidase and tannase are added in amounts which are sufficient to reduce formation of haze caused by storing the tea extract at refrigeration temperatures to an extent substantially greater than that achieved by addition of tannase alone. The amount of tannase added is from 0.25 to 25 activity units and preferably from 0.5 to 10 activity units per gram of soluble tea solids in the extract. An "activity unit" of tannase, as that term is used in this application, is defined as the amount of enzyme that will cause one absorbance unit at 310 micrometers per minute at 30 degrees centigrade in a 1 cm cell using a 0.004% tannic acid solution in 0.02M acetate buffer at pH 4.7. A suitable commercial tannase preparation has 5000 units of activity per gram. The amount of oxidase added is from 1500 to 3750 activity units, preferably from 2250-3000 activity units per grams of soluble tea solids. A "unit" of activity" of glucose oxidase, as that term is used in this application, is defined as the amount of enzyme that will produce one micro mole of hydrogen peroxide in 1 minute at 25 degrees centigrade and pH 7.0. A suitable commercial glucose oxidase preparation has 15,000 units of activity per gram.

The temperature of the tea extract is preferably not more than about 120° F. prior to enzyme addition to minimize deactivation of the enzymes. Temperature during incubation is preferably maintained at about 70°-120° F. and more preferably from 85°-110° F. Incubation is preferably effected for at least about ½ hour, suitably up to 1 to 10 hours. The enzymes are then deactivated by raising the temperature of the tea extract suitably to a temperature of about 125° F. or more for about 10 minutes or more. The tea extract is then passed through solids separation equipment, such as a centrifuge or a filter, to remove insoluble solids.

Following, or concurrent with, enzyme deactivation, the tea extract may be further processed by conventional techniques. For example, the tea extract may be passed to a jacketed batch tank 25 where aroma and flavor components removed during extraction are added back along with other conventional additives, such as flavor, color, water soluble carbohydrates, and preservatives. The water-soluble carbohydrates can include sugars (i.e., sweet-tasting mono and disaccharides), and higher saccharides. Hydrolyzed starch solids such as corn syrup solids, dextrins and maltodextrins are also useful.

Depending upon the desired tea solids concentration in the tea extract, moisture content of the extract can be reduced by suitable methods such as evaporation or reverse osmosis. Generally, the level of soluble tea solids present in the final concentrated tea extract is about 0.3 to 15% by weight of the tea extract. A typical tea beverage contains about 0.50% soluble tea solids. Therefore, in forming a ready-to-drink tea beverage, the required dilution with water will generally range from zero up to about 30:1. Preferably the tea extract is formulated for dilution with water at a ratio of water to extract of about 5-15:1, and more preferably about 8-12:1. A relatively higher level of soluble tea solids is preferred if the extract does not contain any natural or synthetic tea aromas or flavors.

As a final processing step, the tea extract is preferably pasteurized or sterilized and then packed in sterile containers. The packaged tea products are preferably stored under refrigeration. The present process significantly reduces the development of haze in the extracts, particularly in concentrated tea extracts, which would otherwise be induced by such storage under refrigeration. Such concentrates are widely used in restaurants or the like to prepare iced tea beverages. Typically, a quantity of the concentrate is diluted with enough water to make up a batch of iced tea beverage from which several individual servings of iced tea are dispensed. The batch of tea beverage is usually kept refrigerated and may be displayed in a "bubbling" type of dispenser in which the beverage is circulated in a clear vessel and is visible to the consumer. Refrigeration storage temperatures are generally not more than 45° F. and usually from 32°-45° F. As mentioned above, the method of the invention significantly reduces the undesirable haze which would otherwise develop in the refrigerated concentrate or in the refrigerated beverage.

EXAMPLE 1760 parts by weight of boiling distilled water is added to 240 parts of weight of tea leaves in a conventional batch, jacketed extraction vessel and extraction is effected with gentle stirring at 190° F. for 8 minutes. The tea extract is then decanted through US #50 and US #100 sieves to separate the tea extract from the leaves. To 1300 parts by weight of the extract are added:

(1) 1.14 parts by weight tannic acid
(2) 34.5 parts by weight spray dried tea, and
(3) 8.29 parts by weight phosphoric acid The tea extract is slowly stirred for 10 minutes at room temperature and then centrifuged at 13,000 rpm for 10 minutes. The resulting tea extract contains about 6% by weight soluble tea solids based on the weight of the extract. Individual samples are prepared by adding to the tea extract a combination of glucose oxidase in amounts ranging from 0 to 2550 activity units, and tannase in amounts ranging from 0 to 85 activity units per gram of soluble tea solids in the tea extract. The resulting tea extract is then incubated for 2 to 5 hours at 95° F. Each sample tea extract is continuously stirred throughout the incubation period and then refrigerated overnight. The tea extracts are then centrifuged at 13,000 rpm for 10 minutes, decanted, and the supernatants are collected as concentrated tea extract samples.

Clarity of the resulting tea extracts is determined with a Hunter colorimeter and the results are shown in the table below as L/b values, which are directly proportional to clarity. The higher the L/b value, the clearer the product. Concentrations in the Table are given as enzyme activity per gram of soluble tea solids in the tea extracts.

| CLARITY OF TEA BEVERAGES | | | | | | |
|---|---|---|---|---|---|---|
| | | GLUCOSE OXIDASE (Activity per Gram of Soluble Tea Solids) | | | | |
| | | 0 | 2.55 | 25.5 | 255 | 2505 |
| TANNASE | 0 | 4.90 | 5.07 | 4.50 | 4.31 | 5.38 |
| CONC | 0.085 | 6.13 | 6.54 | 4.79 | 4.83 | 6.39 |
| (Activity | 0.85 | 5.87 | 6.19 | 5.31 | 4.42 | 17.51 |
| per Gram of Soluble Tea | 8.5 | 6.74 | 6.50 | 5.01 | 4.00 | 15.26 |
| Solids) | 85 | 7.39 | 7.02 | 6.43 | 5.16 | 7.86 |

By far the greatest clarity is achieved at a glucose oxidase concentration of about 2550 activity units and a tannase concentration of 0.85 and 8.5 activity units per gram of soluble tea solids. The clarity achieved with these particular combinations is much greater (in L/b value) than the clarity achieved using either of the individual enzymes at any concentrations within the tested ranges and is also much greater than when the same two enzymes are used, but at other levels. Tea solids recovery is only slightly lower for extracts treated with both glucose oxidase and tannase than for extracts treated with tannase alone.

Although the invention has been described in considerable detail with respect to preferred embodiments thereof, variations and modifications will be apparent to those skilled in the art without departing from the spirit and scope of the invention as set forth in the claims.

What is claimed is:

1. A process for producing a tea extract which forms a reduced amount of haze when stored under refrigeration comprising the steps of:
   (a) adding oxidase glucose and tannase to a decreamed aqueous tea extract, the amount of added glucose oxidase being from 1500 to 3750 activity units per gram of soluble tea solids in the aqueous tea extract, and the amount of added tannase being from 0.25 to 25 activity units per gram of soluble tea solids in the aqueous tea extract;
   (b) incubating the extract; and
   (c) separating insoluble solids from the incubated extract to provide a tea extract product, the incubating step being carried out for a time sufficient to reduce the formation of haze caused by storing the tea extract product under refrigeration, the reduction in haze being substantially greater than that achievable by incubation with tannase alone.

2. A process according to claim 1 wherein the tea extract product is a concentrate having a concentration of soluble tea solids of about 3–15% by weight based on the weight of the concentrate.

3. A process according to claim 1 wherein the incubating step is effected for at least ½ hour at a temperature of 70° to 120° F.

4. A process according to claim 1 further comprising the steps of chilling the aqueous tea extract at a temperature of not more than 45° F., and separating insoluble solids from the chilled aqueous tea extract before step (a).

5. A process according to claim 1 wherein the step of separating insoluble solids from the incubated tea extract comprises centrifuging the incubated tea extract.

6. A process according to claim 4 wherein the step of separating insoluble solids from the chilled aqueous tea extract comprises centrifuging the chilled tea extract.

7. A process according to claim 1 wherein the tea extract is provided by contacting tea leaves with water at an elevated temperature and separating the resulting aqueous tea extract from the leaves.

8. A process according to claim 7 wherein the tea leaves comprise black tea leaves.

9. A process according to claim 1 wherein the amount of glucose oxidase added is from 2250 to 3000 activity units per gram of soluble tea solids in the tea extract.

10. A process according to claim 9 wherein the amount of tannase added is from 0.5 to 10 activity units per gram of soluble tea solids in the tea extract.

11. A process according to claim 1 wherein the tea extract product is a ready-to-drink beverage containing 0.3 to 1.5% soluble tea solids by weight based on the weight of the tea extract.

12. A process according to claim 2 wherein the tea extract product is formulated for dilution with water at a 5:1 to 15:1 ratio of water to extract to produce, on dilution, a tea beverage having a soluble tea solids content of from 0.3 to 1.5% by weight based on the weight of the beverage.

13. A process for producing a tea extract which forms a reduced amount of haze when stored under refrigeration comprising the steps of:
   (a) contacting tea leaves with water at an elevated temperature to form an aqueous tea extract;
   (b) separating the resulting aqueous tea extract and tea leaves;
   (c) chilling the tea extract;
   (d) separating insoluble solids from the chilled tea extract;
   (e) adding glucose oxidase and tannase to the tea extract, the amount of added glucose oxidase being from 1500 to 3750 activity units per gram of soluble tea solids in the aqueous tea extract, and the amount of added tannase being from 0.25 to 25 activity units per gram of soluble tea solids in the aqueous tea extract;
   (f) incubating the tea extract; and
   (g) separating insoluble solids from the incubated extract to provide a tea extract product, the incubating step being carried out for a time sufficient to reduce formation of haze caused by storing the tea extract product under refrigeration, the reduction in haze being substantially greater than that achievable by incubation with tannase alone.

14. A process according to claim 13 wherein the tea extract product is a concentrate having a soluble tea solid content of from 3–15% by weight based on the weight of the concentrate.

15. A process according to claim 13 wherein in step (a) the temperature of the water is at least 190° F. and contacting is effected for at least 5 minutes.

16. A process according to claim 13 wherein the step of incubating is effected for at least ½ hour at a temperature of 70° to 120° F.

17. A process according to claim 13 wherein the tea extract product is a ready-to-drink beverage having a content of soluble tea solids of from 0.3–1.5% by weight based on the weight of the tea extract product.

18. A process according to claim 13 wherein the amount of glucose oxidase added is from 2250 to 3000 activity units per gram of soluble tea solids in the tea extract, and wherein the amount of tannase added is 0.5 to 10 activity units per gram of soluble tea solids in the tea extract.

19. A process according to claim 13 wherein the step of chilling comprises chilling the tea extract at a temperature of not more than 45° F.

20. A process according to claim 13 wherein step (g) comprises centrifuging the tea extract.

21. A process according to claim 13 wherein the tea extract product is formulated for dilution with water at a 5:1 to 15:1 ratio of water to extract to produce, on dilution, a tea beverage having a soluble tea solids content of from 0.3 to 1.5% by weight based on the weight of the beverage.

* * * * *